United States Patent
Wang

(10) Patent No.: US 10,026,175 B2
(45) Date of Patent: Jul. 17, 2018

(54) IMAGE PROCESSING DEVICE, METHOD, AND RECORDING MEDIUM HAVING AN IMAGE PROCESSING PROGRAM RECORDED THEREIN

(71) Applicant: FUJIFILM Corporation, Tokyo (JP)

(72) Inventor: Caihua Wang, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 135 days.

(21) Appl. No.: 15/052,756

(22) Filed: Feb. 24, 2016

(65) Prior Publication Data
US 2016/0171678 A1 Jun. 16, 2016

Related U.S. Application Data

(63) Continuation of application No. PCT/JP2014/004295, filed on Aug. 21, 2014.

(30) Foreign Application Priority Data

Aug. 26, 2013 (JP) .................... 2013-174365

(51) Int. Cl.
G06K 9/00 (2006.01)
G06T 7/00 (2017.01)
(Continued)

(52) U.S. Cl.
CPC ............ *G06T 7/003* (2013.01); *A61B 6/5235* (2013.01); *G06T 7/0012* (2013.01);
(Continued)

(58) Field of Classification Search
None
See application file for complete search history.

(56) References Cited

U.S. PATENT DOCUMENTS 7,298,869 B1 * 11/2007 Abernathy ........... G06K 9/0063
324/323
8,861,834 B2 * 10/2014 Fujieda ................. B25J 9/1697
382/154
(Continued)

FOREIGN PATENT DOCUMENTS

JP 2002-534204 A 10/2002
JP 2013-141602 A 7/2013
(Continued)

OTHER PUBLICATIONS

Japanese Office Action dated Aug. 30, 2016 with an English translation thereof.
(Continued)

*Primary Examiner* — Nancy Bitar
(74) *Attorney, Agent, or Firm* — McGinn I.P. Law Group, PLLC

(57) ABSTRACT

A three-dimensional common coordinate system is defined and a first correspondence relationship between each pixel of a first three-dimensional image which has at least a portion of a human body as a subject and coordinates on the common coordinate system is set. A second three-dimensional image which has at least a portion of the human body as a subject that at least partially overlaps the subject in the first three-dimensional image is aligned with the first three-dimensional image to calculate a correspondence relationship between pixels of the first three-dimensional image and the second three-dimensional image. A second correspondence relationship between each pixel of the second three-dimensional image and coordinates on the common coordinate system is calculated on the basis of the calculated correspondence relationship and the set first correspondence relationship. The first correspondence relationship and the second correspondence relationship are stored.

14 Claims, 7 Drawing Sheets

(51) Int. Cl.
   *A61B 6/00* (2006.01)
   *G06T 7/30* (2017.01)
   *G06T 7/73* (2017.01)

(52) U.S. Cl.
   CPC .............. *G06T 7/0014* (2013.01); *G06T 7/30* (2017.01); *G06T 7/74* (2017.01); *G06T 2207/10081* (2013.01); *G06T 2207/10088* (2013.01); *G06T 2207/20212* (2013.01); *G06T 2207/30004* (2013.01); *G06T 2207/30196* (2013.01)

(56) References Cited

U.S. PATENT DOCUMENTS

2009/0225099 A1* 9/2009 Yuasa ................ G06T 9/00228
                                                      345/629
2009/0262989 A1* 10/2009 Kozakaya .......... G06K 9/00208
                                                      382/118
2010/0202709 A1   8/2010 Heavens et al.
2013/0177224 A1*  7/2013 Papageorgiou ...... G06K 9/6206
                                                      382/131

FOREIGN PATENT DOCUMENTS

WO   WO 2000/41626 A1   7/2000
WO   WO 2012/069833 A1  5/2012

OTHER PUBLICATIONS

International Search Report (ISR) (PCT Form PCT/ISA/210), in PCT/JP2014/004295, dated Jan. 13, 2015.
International Search Opinion (PCT/ISA/237) in PCT/JP2014/004295, dated Jan. 13, 2015 and a partial English translation thereof.

* cited by examiner

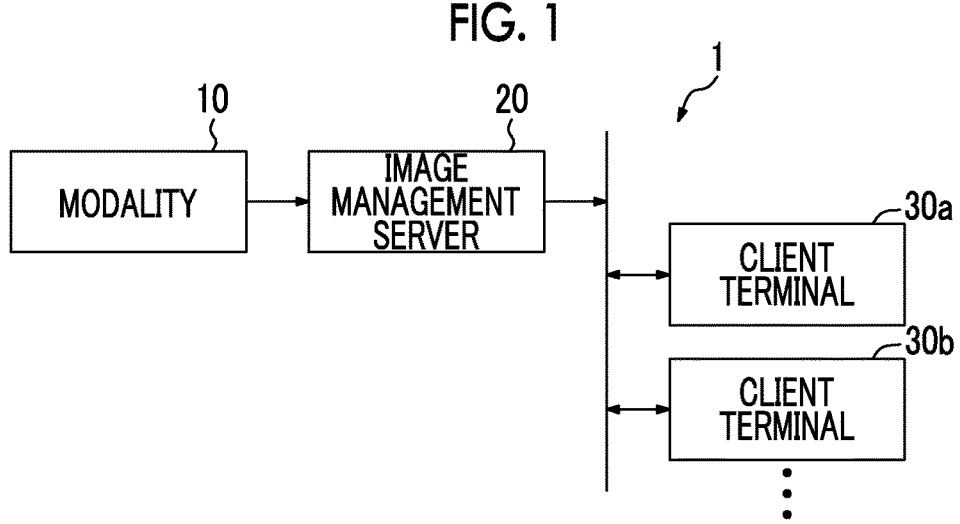
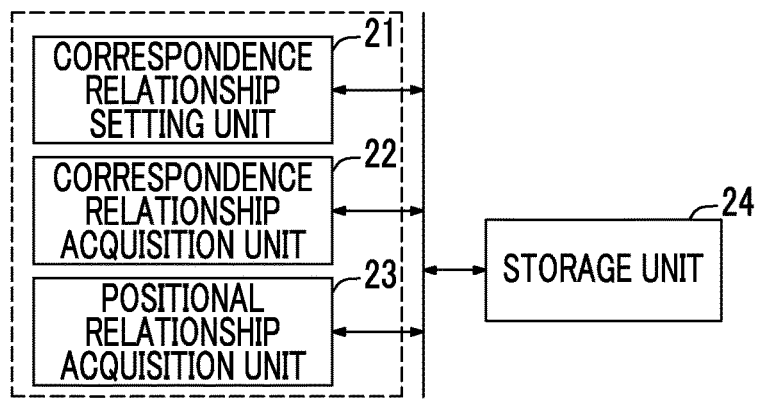
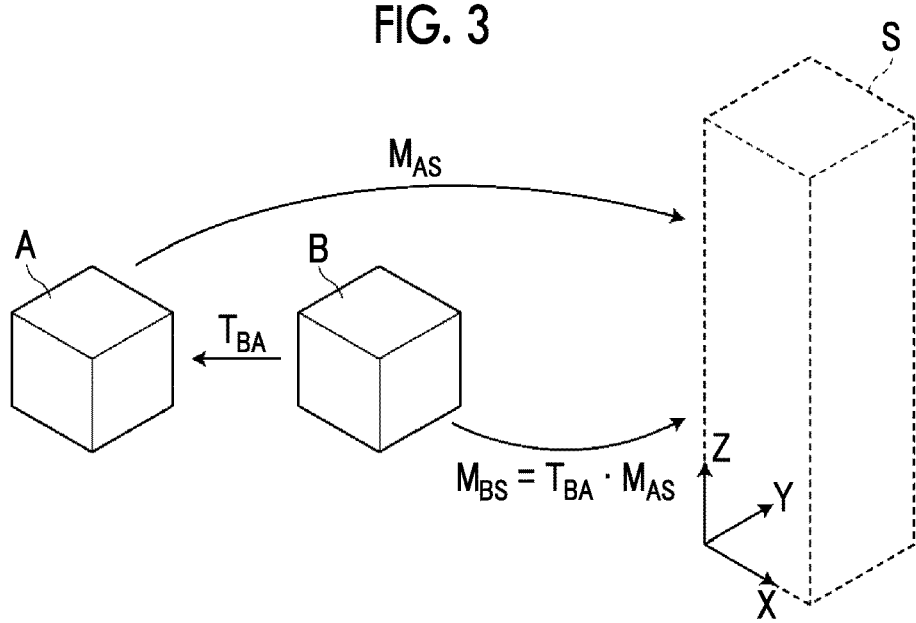

IMAGE PROCESSING DEVICE, METHOD, AND RECORDING MEDIUM HAVING AN IMAGE PROCESSING PROGRAM RECORDED THEREIN

CROSS REFERENCE TO RELATED APPLICATIONS

The present application is a Continuation of PCT International Application No. PCT/JP2014/004295 filed on Aug. 21, 2014, which claims priority under 35 U.S.C. § 119(a) to Japanese Patent Application No. 2013-174365 filed on Aug. 26, 2013. Each of the above applications is hereby expressly incorporated by reference, in its entirety, into the present application.

BACKGROUND OF THE INVENTION

1. Field of the Invention

The present invention relates to an image processing device, method, and recording medium having an image processing program recorded therein, for calculating a positional relationship between captured three-dimensional images of the same patient.

2. Description of the Related Art

In recent years, in the field of medicine, a plurality of captured three-dimensional images of the same patient have been aligned and compared to support diagnosis. It takes a lot of time to calculate the positional relationship between the three-dimensional images. Therefore, it is considered that the positional relationship is calculated for each combination of the three-dimensional images in advance, is stored, and is used for the subsequent calculation process. However, the number of combinations of the three-dimensional images increases exponentially with an increase in the number of three-dimensional images. Therefore, it is not practical to calculate the positional relationships between all of the three-dimensional images and to store the positional relationships.

In contrast, for example, WO2012/069833A and US2010/0202709A disclose a method which, when a plurality of captured three-dimensional images 41 to 45 of the same subject are acquired as illustrated in FIG. 8, uses one three-dimensional image 43 as a reference image, calculates transformation functions $T_1$ to $T_4$ for transformation from the reference image 43 to the other images 41, 42, 44, and 45, stores the transformation functions $T_1$ to $T_4$, and calculates the positional relationship between the three-dimensional images other than the reference image 43 on the basis of the transformation function for transformation from the reference image 43 to each three-dimensional image. For example, as illustrated in FIG. 8, the positional relationship between the three-dimensional images 41 and 44 is calculated by the operation of the transformation function $T_1$ for transformation from the reference image 43 to the three-dimensional image 41 and the transformation function $T_3$ for transformation from the reference image 43 to the three-dimensional image 44.

SUMMARY OF THE INVENTION

In the method disclosed in WO2012/069833A and US2010/0202709A, the three-dimensional images other than the reference image are defined by the transformation functions for transformation from the reference image to the three-dimensional images and the positional relationship between the three-dimensional images is calculated by the operation of the transformation functions. Therefore, it is presumed that each three-dimensional image can be defined by the transformation function from the reference image, that is, each three-dimensional image has the same subject as the reference image. When a three-dimensional image having a subject beyond the range of the subject in the reference image is acquired by the subsequent imaging process, it is difficult to define the three-dimensional image with the transformation function for transformation from the reference image. As a result, it is difficult to calculate the positional relationship between the three-dimensional image and other three-dimensional images using the same method.

For example, as illustrated in FIG. 9, when a CT image 51 of the chest and a CT image 52 of the chest and abdomen are acquired from the same patient, it is considered that the CT image 52 of the chest and abdomen is used as a reference image and a transformation function $T_1$ for transformation from the reference image 52 to the CT image 51 is calculated and stored. When a CT image 53 of the whole body and a CT image 54 of the head and neck are further acquired by the subsequent imaging process, it is difficult to define the CT image 53 or the CT image 54 with the transformation function for transformation from the reference image 52. Therefore, in the method using the transformation function for transformation from the reference image, it is difficult to calculate the positional relationship between the CT image 53 or the CT image 54 and other images.

In this case, for example, the following method is considered. As illustrated in FIG. 9, the CT image 53 of the whole body is used as a second reference image and a relation function $T_P$ between the reference images 52 and 53 and a transformation function $T_2$ for transformation from the second reference image 53 to the CT image 54 is calculated and stored. The positional relationship between the CT images 51 and 54 which are defined by only a transformation function for transformation from another reference image is calculated, using a relation function $T_P$ between the reference images in addition to the transformation functions $T_1$ and $T_2$ for transformation from each reference image. However, this method has the problem that calculation becomes complicated and the total amount of calculation is large.

The invention has been made in view of the above-mentioned problems and an object of the invention is to provide an image processing device, method, and program which can effectively calculate a positional relationship between a plurality of three-dimensional images.

An image processing device, method, and program according to the invention is based on the idea that, when a three-dimensional coordinate system is defined, it is possible to define a three-dimensional space with a sufficient size to include the whole body of a patient on the coordinate system, that is, each pixel of the three-dimensional image indicating the three-dimensional space can be associated with coordinates on the coordinate system. The image processing device, method, and program calculates a correspondence relationship between each captured three-dimensional image of the patient and the coordinate system, stores the correspondence relationship, and calculates a positional relationship between the three-dimensional images on the basis of the relationship between each image and the coordinate system.

According to an aspect of the invention, there is provided an image processing device including: correspondence relationship setting means for setting a three-dimensional common coordinate system and for setting a first correspondence relationship between each pixel of a first three-dimensional image which has at least a portion of a human body as a subject and coordinates on the common coordinate system; correspondence relationship acquisition means for aligning a second three-dimensional image, which has at least a portion of the human body as a subject that at least partially overlaps the subject in the first three-dimensional image, with the first three-dimensional image to calculate a correspondence relationship between pixels of the first three-dimensional image and the second three-dimensional image, and for calculating a second correspondence relationship between each pixel of the second three-dimensional image and coordinates on the common coordinate system, on the basis of the calculated correspondence relationship and the set first correspondence relationship; and storage means for storing the first correspondence relationship and the second correspondence relationship.

The image processing device according to the above-mentioned aspect may further include positional relationship acquisition means for calculating a positional relationship between the three-dimensional images whose correspondence relationship with the coordinates on the common coordinate system has been stored in the storage means, using an operation of the correspondence relationships between the three-dimensional images stored in the storage means.

In the image processing device according to the above-mentioned aspect, the correspondence relationship acquisition means may align a new three-dimensional image, which has at least a portion of the human body as a subject that at least partially overlaps the subject in the existing three-dimensional image whose correspondence relationship has been stored in the storage means, with the existing three-dimensional image to calculate a correspondence relationship between pixels of the existing three-dimensional image and the new three-dimensional image, and may calculate a third correspondence relationship between each pixel of the new three-dimensional image and coordinates on the common coordinate system, on the basis of the calculated correspondence relationship and the correspondence relationship of the existing three-dimensional image stored in the storage means. The storage means may store the calculated third correspondence relationship.

The correspondence relationship acquisition means may calculate a correspondence relationship between a portion of the entire new three-dimensional image in which the subject overlaps the subject in the existing three-dimensional image and coordinates on the common coordinate system, using an operation of at least portions of the correspondence relationship between the pixels of the existing three-dimensional image and the new three-dimensional image and the correspondence relationship of the existing three-dimensional image stored in the storage means. The correspondence relationship acquisition means may extrapolate the correspondence relationship of the overlap portion to calculate a correspondence relationship between a portion of the entire new three-dimensional image in which the subject does not overlap the subject in the existing three-dimensional image and coordinates on the common coordinate system.

The correspondence relationship setting means may set a correspondence relationship in which a relative positional relationship between the pixels of the first three-dimensional image is the same as a relative positional relationship between the coordinates associated with each of the pixels on the common coordinate system as the first correspondence relationship.

In the image processing device according to the above-mentioned aspect, the correspondence relationship setting means may define a three-dimensional auxiliary coordinate system and may set a fourth correspondence relationship between each pixel of a fourth three-dimensional image having a subject which does not overlap any subjects in the three-dimensional images whose correspondence relationship with the coordinates on the common coordinate system has been stored in the storage means and coordinates on the auxiliary coordinate system. The correspondence relationship acquisition means may align a fifth three-dimensional image having a subject which does not overlap any subjects in the three-dimensional images whose correspondence relationship with the coordinates on the common coordinate system has been stored in the storage means and at least partially overlaps the subject in the fourth three-dimensional image to calculate a correspondence relationship between pixels of the fourth three-dimensional image and the fifth three-dimensional image, and may calculate a fifth correspondence relationship between each pixel of the fifth three-dimensional image and coordinates on the auxiliary coordinate system, on the basis of the calculated correspondence relationship and the set fourth correspondence relationship. The storage means may store the fourth correspondence relationship and the fifth correspondence relationship. The positional relationship acquisition means may calculate a positional relationship between the three-dimensional images whose correspondence relationship with the coordinates on the common coordinate system has not been stored and whose correspondence relationship with coordinates on the auxiliary coordinate system has been stored, using an operation of the correspondence relationships between the three-dimensional images and the coordinates on the auxiliary coordinate system which are stored in the storage means.

When a subject in a new three-dimensional image whose correspondence relationship with coordinates on the common coordinate system has been stored in the storage means at least partially overlaps the subject in the existing three-dimensional image whose correspondence relationship with coordinates on the auxiliary coordinate system has been stored in the storage means, the correspondence relationship acquisition means may align the existing three-dimensional image with the new three-dimensional image to calculate a correspondence relationship between pixels of the existing three-dimensional image and the new three-dimensional image, and may calculate a sixth correspondence relationship between each pixel of the existing three-dimensional image and coordinates on the common coordinate system, on the basis of the calculated correspondence relationship and the correspondence relationship between the new three-dimensional image and the coordinates on the common coordinate system stored in the storage means. The storage means may store the calculated sixth correspondence relationship, instead of the stored correspondence relationship between the existing three-dimensional image and the coordinates on the auxiliary coordinate system.

According to another aspect of the invention, there is provided an image processing method that is performed by an image processing device including correspondence relationship setting means, correspondence relationship acquisition means, and storage means. The method includes: allowing the correspondence relationship setting means to set a three-dimensional common coordinate system and to set a first correspondence relationship between each pixel of a first three-dimensional image which has at least a portion of a human body as a subject and coordinates on the common coordinate system; allowing the correspondence relationship acquisition means to align a second three-dimensional image, which has at least a portion of the human body as a subject that at least partially overlaps the subject in the first three-dimensional image, with the first three-dimensional image to calculate a correspondence relationship between pixels of the first three-dimensional image and the second three-dimensional image, and to calculate a second correspondence relationship between each pixel of the second three-dimensional image and coordinates on the common coordinate system, on the basis of the calculated correspondence relationship and the set first correspondence relationship; and allowing the storage means to store the first correspondence relationship and the second correspondence relationship.

According to still another aspect of the invention, there is provided an image processing program that causes a computer to function as: correspondence relationship setting means for setting a three-dimensional common coordinate system and for setting a first correspondence relationship between each pixel of a first three-dimensional image which has at least a portion of a human body as a subject and coordinates on the common coordinate system; correspondence relationship acquisition means for aligning a second three-dimensional image, which has at least a portion of the human body as a subject that at least partially overlaps the subject in the first three-dimensional image, with the first three-dimensional image to calculate a correspondence relationship between pixels of the first three-dimensional image and the second three-dimensional image, and for calculating a second correspondence relationship between each pixel of the second three-dimensional image and coordinates on the common coordinate system, on the basis of the calculated correspondence relationship and the set first correspondence relationship; and storage means for storing the first correspondence relationship and the second correspondence relationship.

In general, the image processing program includes a plurality of program modules and the function of each of the above-mentioned means is implemented by one program module or a plurality of program modules. These program module groups are recorded on a recording medium, such as a CD-ROM or a DVD, or are recorded so as to be downloaded to a storage attached to a server computer or a network storage and are then provided to the user.

According to the image processing device, method, and program of the invention, a three-dimensional common coordinate system is set and a first correspondence relationship between each pixel of a first three-dimensional image which has at least a portion of a human body as a subject and coordinates on the common coordinate system is set. A second three-dimensional image, which has at least a portion of the human body as a subject that at least partially overlaps the subject in the first three-dimensional image, is aligned with the first three-dimensional image to calculate a correspondence relationship between pixels of the first three-dimensional image and the second three-dimensional image. A second correspondence relationship between each pixel of the second three-dimensional image and coordinates on the common coordinate system is calculated on the basis of the calculated correspondence relationship and the set first correspondence relationship. The first correspondence relationship and the second correspondence relationship are stored. Therefore, when the positional relationship between the first three-dimensional image and the second three-dimensional image is calculated later, it is possible to effectively calculate the positional relationship between target three-dimensional images, using an operation of the correspondence relationships between the three-dimensional images and the common coordinate system stored in the storage unit.

BRIEF DESCRIPTION OF THE DRAWINGS

FIG. 1 is a diagram schematically illustrating the structure of an image processing system to which an image processing device according to the invention is introduced.

FIG. 2 is a functional block diagram illustrating an image management server.

FIG. 3 is a diagram illustrating a process for calculating the positional relationship between the captured images of the same subject.

DESCRIPTION OF THE PREFERRED EMBODIMENTS

Figure 4:
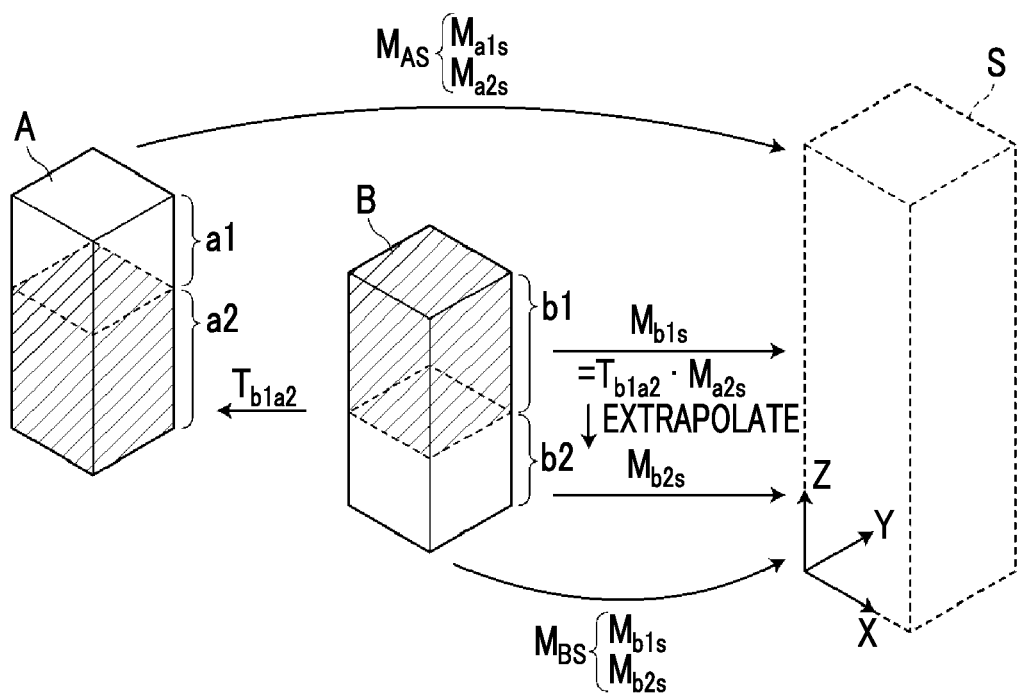
FIG. 4 is a diagram illustrating a process for calculating the positional relationship between images in which subjects partially overlap each other.

Hereinafter, an image processing system to which an image processing device according to an embodiment of the invention is introduced will be described. FIG. 1 is a diagram schematically illustrating the structure of an image processing system 1. As illustrated in FIG. 1, the system 1 includes, for example, a modality 10, an image management server 20, and client terminals 30 (30a, 30b, . . . ). The components forming the image processing system 1 are connected to each other through a network. In this embodiment, each means of the image processing device according to the invention is formed by the image management server 20.

The modality 10 is a device which captures the images of a part of the patient to be examined, generates a three-dimensional image (image data) of the part, and outputs the three-dimensional image, and is, for example, a CT or MRI device.

The image management server 20 is a computer that stores and manages the three-dimensional image (image data) acquired by the modality 1, searches for image data in response to a browsing request from the client terminal 30, and transmits the extracted image data to the client terminal 30 which is a request source, and includes, for example, a central processing unit (CPU), a memory, a hard disk in which a database management program or an image processing program according to this embodiment is installed, and a storage. The CPU of the computer executes the image processing program to implement, for example, a correspondence relationship setting process, a correspondence relationship acquisition process, a positional relationship acquisition process, and a storage process.

The client terminal 30 (30a, 30b, . . . ) is a computer which is used by an operator, such as a doctor, to browse an image. In the client terminal 30, processes, such as a process of requesting the image management server 20 to browse an image, a process of requesting the transmission of information about the positional relationship between a plurality of specific images, and a process of displaying the image or information received from the image management server 20, are performed by the execution of a software program for performing these processes.

FIG. 2 is a block diagram illustrating the divided functional levels of the image management server 20. As illustrated in FIG. 2, the image management server 20 includes, for example, a correspondence relationship setting unit 21, a correspondence relationship acquisition unit 22, a positional relationship acquisition unit 23, and a storage unit 24. The CPU executes the image processing program to implement the functions of each functional unit in a frame indicated by a dashed line and the storage unit 24 is implemented by a storage.

The storage unit 24 sequentially stores the three-dimensional images acquired by the modality 1. In a stage in which two or more three-dimensional images of a certain patient are acquired and stored, first, the correspondence relationship setting unit 21 defines a three-dimensional common coordinate system S for the patient. Here, the common coordinate system S can define a three-dimensional space with a sufficient size to include the entire body of the patient on the coordinate system. In the common coordinate system S, each pixel of a three-dimensional image indicating the three-dimensional space can be associated with coordinates on the coordinate system.

The correspondence relationship setting unit 21 selects any one (first three-dimensional image) of the three-dimensional images of the patient and sets a first correspondence relationship between each pixel of the selected first three-dimensional image and coordinates on the common coordinate system S. Specifically, the correspondence relationship setting unit 21 sets a mapping function indicating the first correspondence relationship. In this embodiment, the set mapping function is stored in the storage unit 24.

Any function which can define the correspondence relationship in which each pixel of the first three-dimensional image is associated with different coordinates on the common coordinate system S can be set as the mapping function indicating the first correspondence relationship. In this case, a linear mapping in which the relative positional relationship between the pixels of the first three-dimensional image is the same as the relative positional relationship between the coordinates associated with each pixel on the common coordinate system S can be set as the mapping function indicating the first correspondence relationship. For example, a linear mapping in which the coordinates of each pixel of the first three-dimensional image on the common coordinate system S when the first three-dimensional image is arranged at a reference position on the common coordinate system S and the entire image is arbitrarily enlarged, reduced, or shifted are associated with each pixel can be set as the mapping function indicating the first correspondence relationship.

In addition, a non-linear mapping may be set as the mapping function indicating the first correspondence relationship. For example, when another three-dimensional image (second three-dimensional image B) having the same part of the same patent as the first three-dimensional image A is acquired, a transformation function $T_{BA}$ from transformation from the second three-dimensional image B to the first three-dimensional image A can be calculated and a non-linear mapping can be defined on the basis of the transformation function $T_{BA}$. Then, the defined mapping can be set as a mapping function $M_{AS}$ indicating the first correspondence relationship. For example, a $(\frac{1}{2}) \times T_{AB}$ mapping can be set as the mapping function $M_{AS}$.

As described above, after the correspondence relationship between any one of the three-dimensional images of the patient and the common coordinate system S is set, the correspondence relationship acquisition unit 22 sequentially acquires the correspondence relationships between other three-dimensional images of the same patient and the common coordinate system S, on the basis of the information of the set correspondence relationship. The correspondence relationship acquisition unit 22 aligns each three-dimensional image (hereinafter, referred to as a new three-dimensional image), in which the subject partially overlaps that in the three-dimensional image (hereinafter, referred to as the existing three-dimensional image) whose correspondence relationship with the common coordinate system S has been acquired and stored in the storage unit 24 and whose correspondence relationship with the common coordinate system S has not been acquired, with the existing three-dimensional image to calculate the correspondence relationship between the pixels of the existing three-dimensional image and the new three-dimensional image, and calculates the correspondence relationship between each pixel of the new three-dimensional image and coordinates on the common coordinate system S, on the basis of the calculated correspondence relationship and the correspondence relationship between the existing three-dimensional image and the common coordinate system S. Specifically, the correspondence relationship acquisition unit 22 calculates a mapping function indicating the correspondence relationship. The calculated mapping function is stored in the storage unit 24. A non-rigid registration method may be used for the alignment between the three-dimensional images.

In particular, when there is a portion of the new three-dimensional image in which the subject does not overlap any subjects in the existing three-dimensional images, the correspondence relationship between a portion of the entire new three-dimensional image in which the subject overlaps the subjects in the existing three-dimensional images and the common coordinate system S is calculated by the operation of the correspondence relationship between the pixels of the existing three-dimensional image and the new three-dimensional image and the correspondence relationship between the existing three-dimensional image and the common coordinate system S. The correspondence relationship between a portion of the entire new three-dimensional image in which the subject does not overlap any subjects in the existing three-dimensional images and the common coordinate system S is calculated by extrapolating the correspondence relationship of the overlap portion.

Then, the positional relationship acquisition unit 23 calculates the positional relationship between the three-dimensional images whose correspondence relationship with the coordinates on the common coordinate system S has been stored in the storage unit 24, using the operation of the correspondence relationships (mapping functions) between the three-dimensional images stored in the storage unit 24, in response to, for example, a request from the client terminal 30, and provides information about the calculated positional relationship to the client terminal 30 which is a request source.

For example, as illustrated in FIG. 3, two three-dimensional images A and B having the same part (the same subject) of the same patient are acquired. The correspondence relationship setting unit 21 sets a mapping function $M_{AS}$ indicating the correspondence relationship between the three-dimensional image A and the common coordinate system S. When the mapping function $M_{AS}$ is stored in the storage unit 24, the correspondence relationship acquisition unit 22 aligns the three-dimensional images A and B to calculate a transformation function $T_{BA}$ (a transformation function for transformation from the three-dimensional image B to the three-dimensional image A) indicating the correspondence relationship between the pixels of the three-dimensional images A and B, and calculates a mapping function $M_{BS}$ ($=T_{BA} \cdot M_{AS}$) indicating the correspondence relationship between the three-dimensional image B and the common coordinate system S, using the operation of the calculated transformation function $T_{BA}$ and the mapping function $M_{AS}$. The storage unit 24 stores only the mapping function $M_{BS}$ in addition to the mapping function $M_{AS}$. When a positional relationship $T_{AB}$ (or $T_{BA}$) between the three-dimensional images A and B is calculated later, the positional relationship acquisition unit 23 reads the mapping function $M_{AS}$ and the mapping function $M_{BS}$ stored in the storage unit 24 and calculates the positional relationship $T_{AB}$ ($=M_{AS} \cdot M_{BS}^{-1}$) between the three-dimensional images A and B using the operation of the mapping functions.

For example, as illustrated in FIG. 4, two three-dimensional images A and B having an overlap part of the subject are acquired. The correspondence relationship setting unit 21 sets a mapping function $M_{AS}$ indicating the correspondence relationship between the three-dimensional image A and the common coordinate system S. When the mapping function $M_{AS}$ is stored in the storage unit 24, the correspondence relationship acquisition unit 22 aligns portions of the three-dimensional images A and B in which the subjects overlap each other (a region a2 of the three-dimensional image A and a region b1 of the three-dimensional image B) to calculate a transformation function $T_{b1a2}$ (a transformation function for transformation from the region b1 to the region a2) indicating the correspondence relationship between the pixels of the region a2 and the region b1, and calculates a mapping function $M_{b1S}$ ($=T_{b1a2} \cdot M_{a2S}$) indicating the correspondence relationship between the region b1 and the common coordinate system S, using the operation of the calculated transformation function $T_{b1a2}$ and a portion $M_{a2S}$ related to the region a2 in the mapping function $M_{AS}$. Then, the correspondence relationship acquisition unit 22 extrapolates the calculated mapping function $M_{b1S}$ to calculate a mapping function $M_{b2S}$ indicating the correspondence relationship between a region b2 and the common coordinate system S. Then, the correspondence relationship acquisition unit 22 integrates the mapping functions $M_{b1S}$ and $M_{b2S}$ into one mapping function $M_{BS}$ indicating the correspondence relationship between the three-dimensional image B and the common coordinate system S.

Then, similarly to the case illustrated in FIG. 3, in addition to the mapping function $M_{AS}$, only the mapping function $M_{BS}$ is stored in the storage unit 24. When the positional relationship $T_{AB}$ (or $T_{BA}$) between the three-dimensional images A and B are calculated later, the positional relationship acquisition unit 23 reads the mapping function $M_{AS}$ and the mapping function $M_{BS}$ stored in the storage unit 24 and calculates the positional relationship $T_{AB}$ ($=M_{AS} \cdot M_{BS}^{-1}$) between the three-dimensional images A and B, using the operation of the mapping functions.

Figure 5:
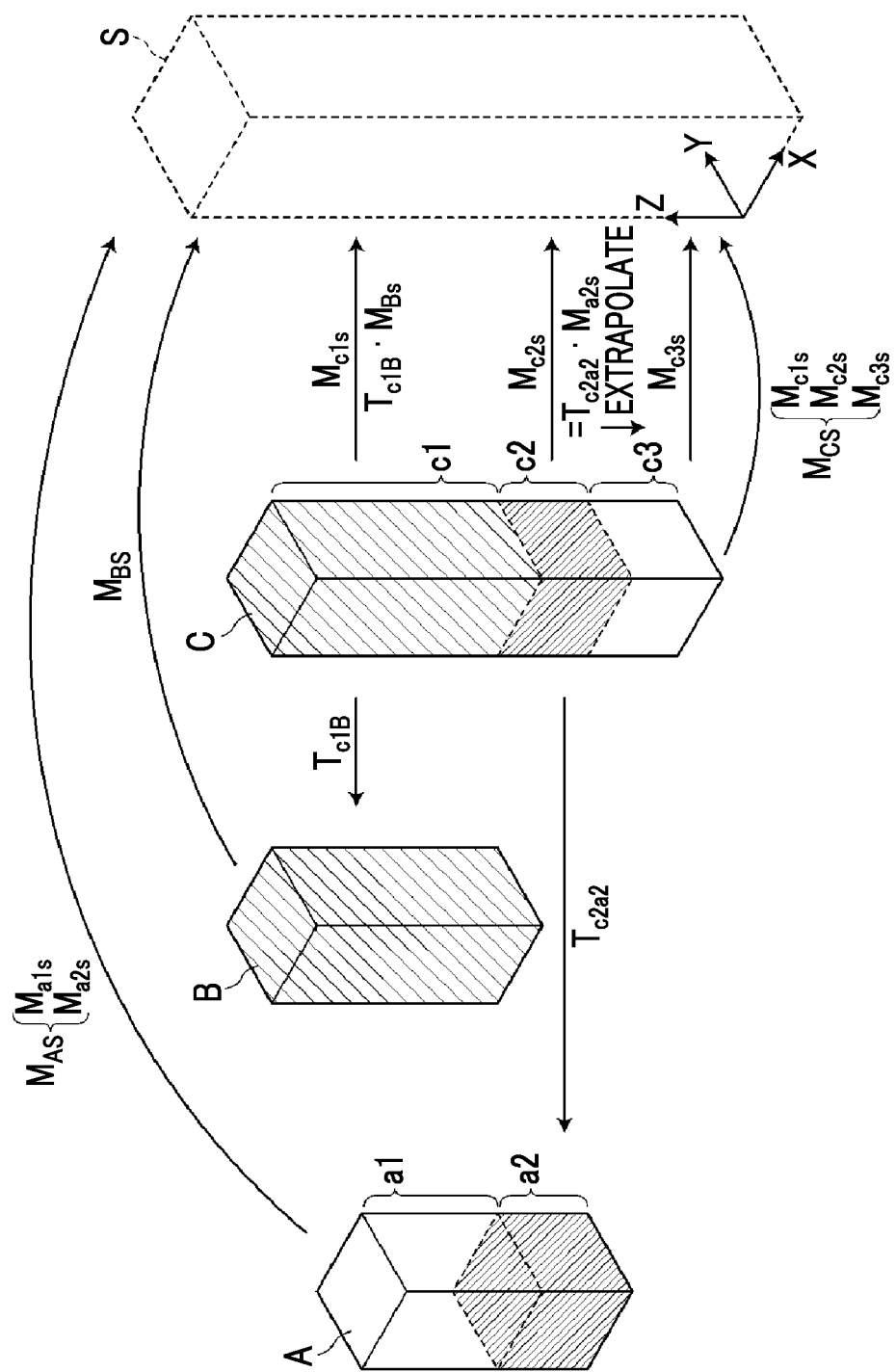
FIG. 5 is a diagram illustrating a process for calculating the positional relationship between images when three or more images are acquired.

For example, as illustrated in FIG. 5, three three-dimensional images A, B, and C are sequentially acquired. When mapping functions $M_{AS}$ and $M_{BS}$ indicating the correspondence relationships between the three-dimensional images A and B and the common coordinate system S are stored in the storage unit 24, first, the correspondence relationship acquisition unit 22 specifies the three-dimensional image B having the subject which overlaps that in the three-dimensional image C in the widest range, aligns portions (the entire three-dimensional image B and a region c1 of the three-dimensional image C) of the three-dimensional images B and C in which the subjects overlap each other to calculate a transformation function $T_{c1B}$ (a transformation function for transformation from the region c1 to the three-dimensional image B) indicating the correspondence relationship between the pixels of the entire three-dimensional image B and the region c1, and calculates a mapping function $M_{c1S}$ ($=T_{c1B} \cdot M_{BS}$) indicating the correspondence relationship between the region c1 and the common coordinate system S, using the operation of the calculated transformation function $T_{c1B}$ and the mapping function $M_{BS}$.

Then, the correspondence relationship acquisition unit 22 aligns the remaining region of the three-dimensional image C and a portion of the three-dimensional image A in which the subjects overlap each other (a region a2 of the three-dimensional image A and a region c2 of the three-dimensional image C) to calculate a transformation function $T_{c2a2}$ (a transformation function for transformation from the region c2 to the region a2) indicating the correspondence relationship between the pixels of the region a2 and the region c2, and calculates a mapping function $M_{c2S}$ ($=T_{c2a2} \cdot M_{a2S}$) indicating the correspondence relationship between the region c1 and the common coordinate system S, using the operation of the calculated transformation function $T_{c2a2}$ and a portion $M_{a2S}$ related to the region a2 in the mapping function $M_{AS}$. Then, the correspondence relationship acquisition unit 22 extrapolates the calculated mapping function $M_{c2S}$ to calculate a mapping function $M_{c3S}$ indicating the correspondence relationship between a region c3 and the common coordinate system S, and integrates the mapping functions $M_{c1S}$, $M_{c2S}$, and $M_{c3S}$ into one mapping function $M_{CS}$ indicating the correspondence relationship between the three-dimensional image C and the common coordinate system S.

Then, in addition to the mapping functions $M_{AS}$ and $M_{BS}$, only the mapping function $M_{CS}$ is stored in the storage unit 24. When the positional relationship between the three-dimensional images A and B, the positional relationship between the three-dimensional images B and C, or the positional relationship between the three-dimensional images C and A is calculated later, the positional relationship acquisition unit 23 reads the mapping functions for the three-dimensional images which are stored in the storage unit 24 and calculates the positional relationship between the three-dimensional images, using the operation of the mapping functions, similarly to the cases illustrated in FIGS. 3 and 4.

The image management server 20 may start, for example, a correspondence relationship setting process (various processes according to the invention) first after a three-dimensional image having the subject which overlaps that in any one of the other acquired three-dimensional images, or may start, for example, the correspondence relationship setting process at the position where any three-dimensional image is acquired.

Figure 6:
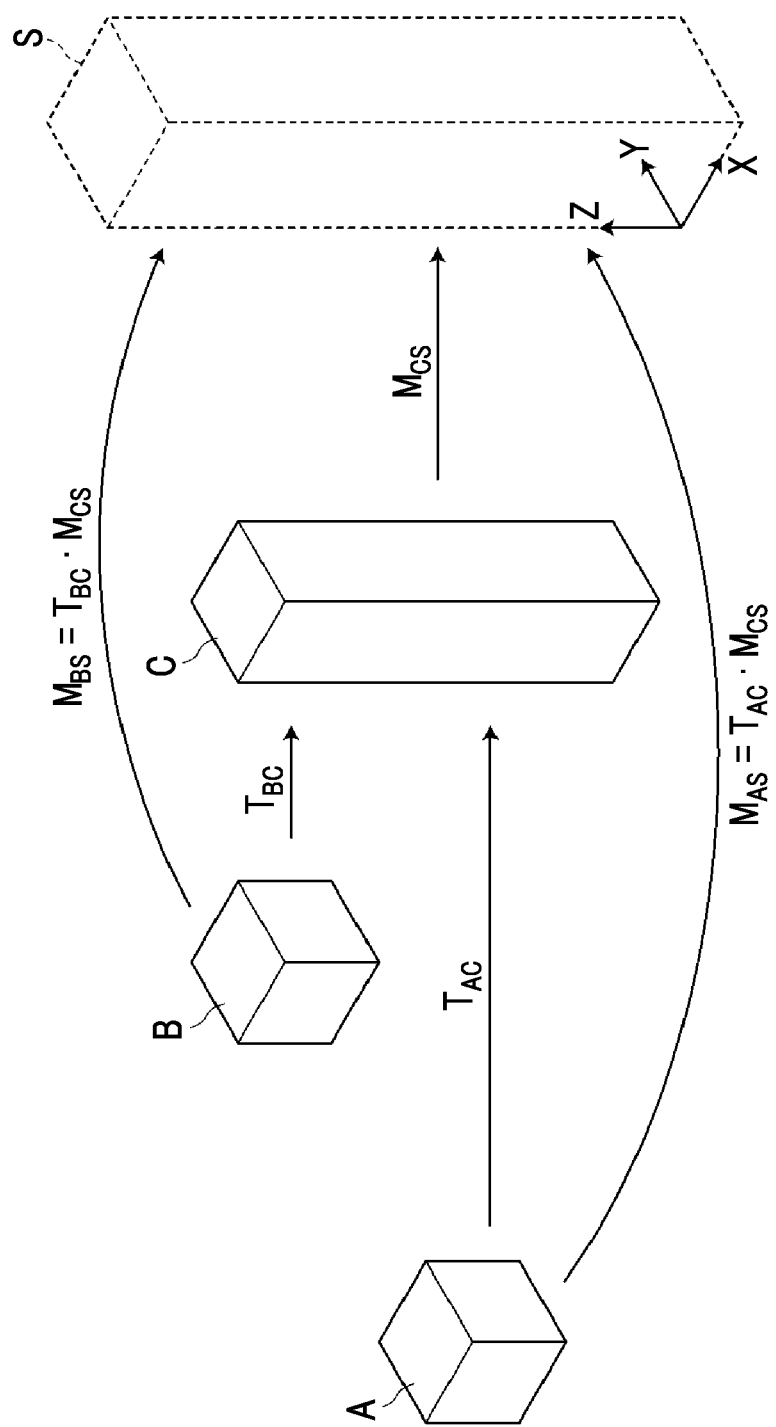
FIG. 6 is a diagram illustrating a process for calculating the positional relationship between images when the images in which subjects overlap each other and the images in which subjects do not overlap each other are sequentially acquired.

For example, in the former case, as illustrated in FIG. 6, when two three-dimensional images A and B in which the subjects do not overlap each other and the three-dimensional image C having the subject which at least partially overlaps those in the three-dimensional images A and B are acquired in the order of, A, B, and C, the correspondence relationship setting unit 21 may wait without starting, for example, the correspondence relationship setting process in the stage in which the three-dimensional image A and the three-dimensional image B are acquired. In the stage in which the three-dimensional image C is acquired, the correspondence relationship setting unit 21 may set first a mapping function $M_{CS}$ indicating the correspondence relationship between the common coordinate system S and the three-dimensional image C having the subject which overlaps those in other three-dimensional images in the widest range among the acquired three-dimensional images.

Then, the correspondence relationship acquisition unit 22 aligns the three-dimensional images A and C to calculate a transformation function $T_{AC}$ (a transformation function for transformation from the three-dimensional image A to the three-dimensional image C) indicating the correspondence relationship between the pixels of the three-dimensional images A and C, and calculates a mapping function $M_{AS}$ ($=T_{AC} \cdot M_{CS}$) indicating the correspondence relationship between the three-dimensional image A and the common coordinate system S, using the operation of the calculated transformation function $T_{AC}$ and the mapping function $M_{CS}$. In addition, the correspondence relationship acquisition unit 22 aligns the three-dimensional images B and C to calculate a transformation function $T_{BC}$ (a transformation function for transformation from the three-dimensional image B to the three-dimensional image C) indicating the correspondence relationship between the pixels of the three-dimensional images B and C, and calculates a mapping function $M_{BS}$ ($=T_{BC} \cdot M_{CS}$) indicating the correspondence relationship between the three-dimensional image B and the common coordinate system S, using the operation of the calculated transformation function $T_{BC}$ and the mapping function $M_{CS}$.

Then, only the mapping functions $M_{AS}$, $M_{BS}$, and $M_{CS}$ are stored in the storage unit 24. When the positional relationship between the three-dimensional images A and B, the positional relationship between the three-dimensional images B and C, or the positional relationship between the three-dimensional images C and A is calculated later, the positional relationship acquisition unit 23 reads the mapping functions for the three-dimensional images which are stored in the storage unit 24 and calculates the positional relationship between the three-dimensional images, using the operation of the mapping functions, similarly to the cases illustrated in FIGS. 3 to 5.

When a three-dimensional image having the subject which does not overlap any subjects in the three-dimensional images whose correspondence relationship with the coordinates on the common coordinate system has been stored in the storage unit 24 is acquired, the image management server 20 calculates the correspondence relationship between the acquired three-dimensional image and the coordinates on the common coordinate system after the subject in the acquired three-dimensional image at least partially overlaps the subjects in the three-dimensional images whose correspondence relationship with the coordinates on the common coordinate system has been stored in the storage unit 24 later. In this case, until the subjects at least partially overlap each other, the image management server 20 may be in a standby state without performing, for example, the correspondence relationship setting process for the three-dimensional image, or may calculate the positional relationship between the three-dimensional image and another three-dimensional image in which the subjects overlap each other, using a three-dimensional auxiliary coordinate system S' which is separately defined.

Figure 7:
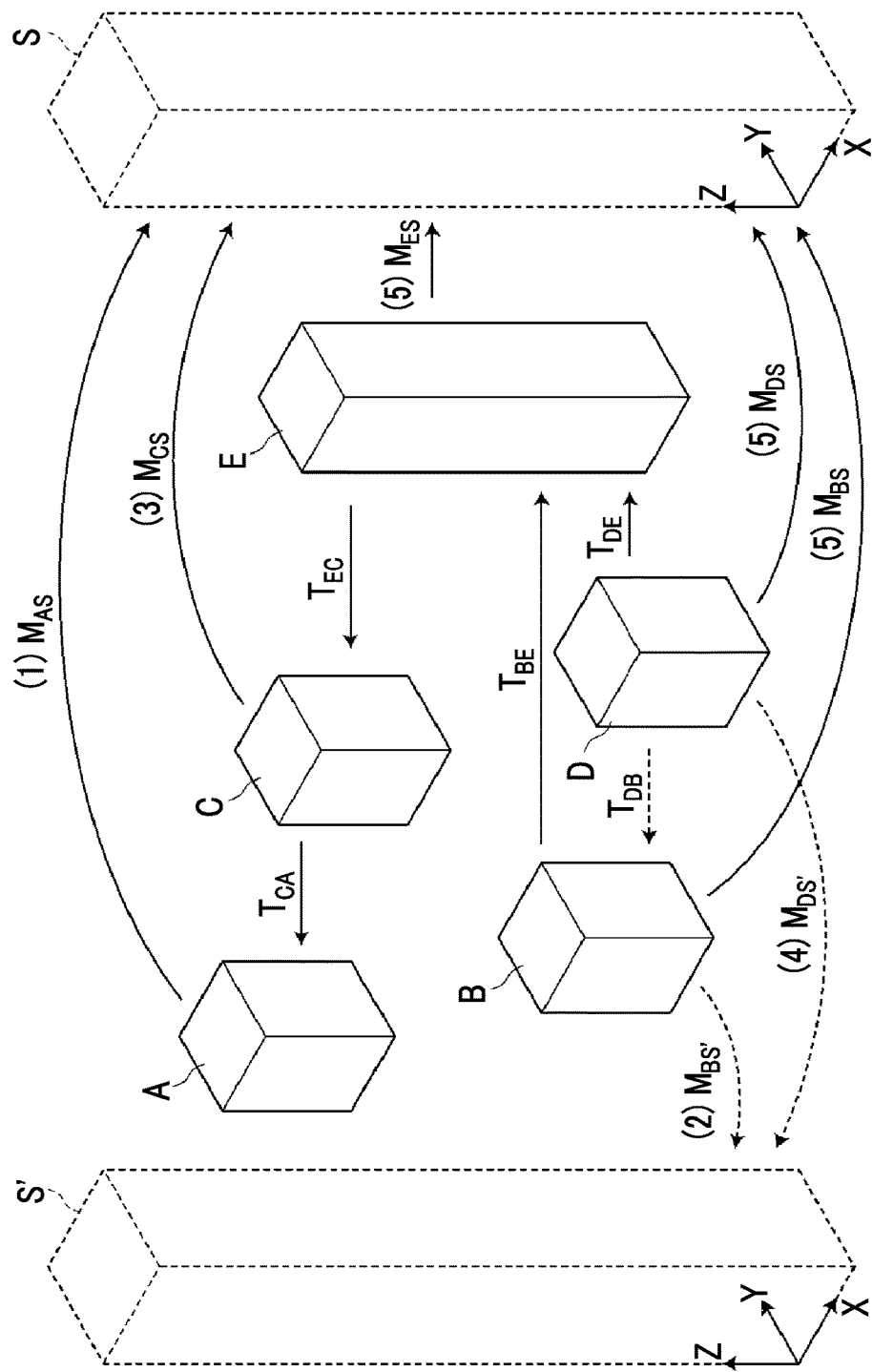
FIG. 7 is a diagram illustrating a process using an auxiliary coordinate system.
Figure 8:
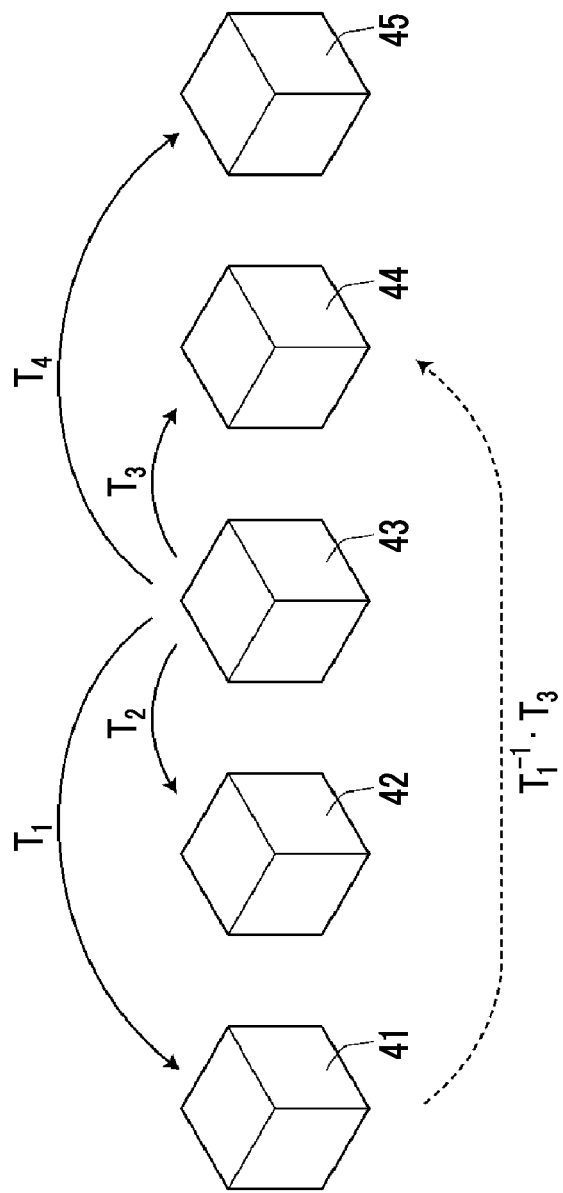
FIG. 8 is a diagram illustrating the related art.
Figure 9:
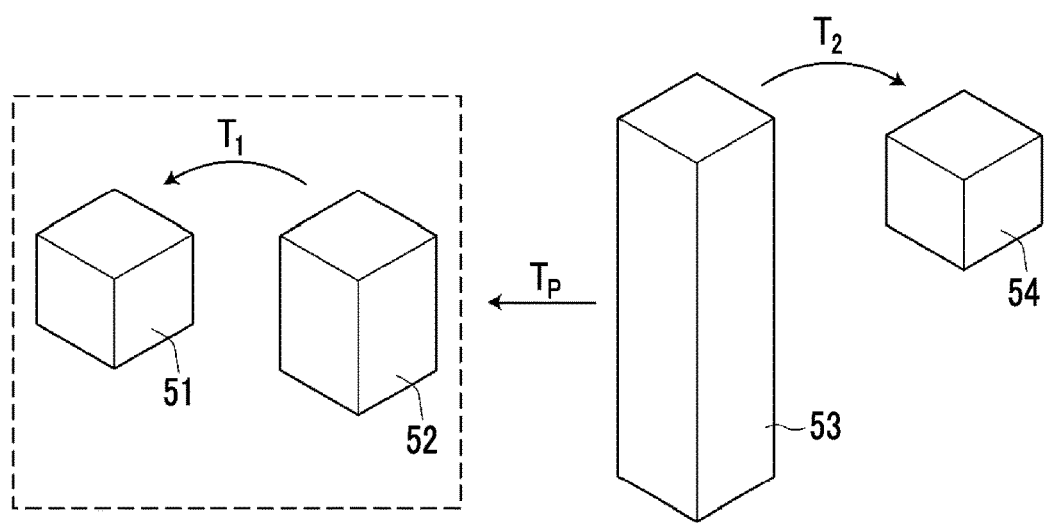
FIG. 9 is a diagram illustrating the problems to be solved.

For example, as illustrated in FIG. 7, in a case in which five three-dimensional images A, B, C, D, and E are sequentially acquired, first, in a stage in which the three-dimensional image A is acquired, the correspondence relationship setting unit 21 sets a mapping function $M_{AS}$ indicating the correspondence relationship between the three-dimensional image A and the common coordinate system S and stores the mapping function $M_{AS}$ in the storage unit 24 (1). Then, when the three-dimensional image B is acquired, the correspondence relationship setting unit 21 sets a mapping function $M_{BS'}$ indicating the correspondence relationship between the three-dimensional image B and the auxiliary coordinate system S' and stores the mapping function $M_{BS'}$ in the storage unit 24 since the subject in the three-dimensional image B does not overlap the subject in the three-dimensional image A (2). Then, when the three-dimensional image C is acquired, the correspondence relationship acquisition unit 22 aligns the three-dimensional images A and C to calculate a transformation function $T_{CA}$ indicating the correspondence relationship between the pixels of the three-dimensional images A and C, calculates a mapping function $M_{CS}$ ($=T_{CA} \cdot M_{AS}$) indicating the correspondence relationship between the three-dimensional image C and the common coordinate system S, using the operation of the calculated transformation function $T_{CA}$ and the mapping function $M_{AS}$, and stores the mapping function $M_{CS}$ in the storage unit 24 since the subject in the three-dimensional image C at least partially overlaps the subject in the three-dimensional image A (3).

Then, when the three-dimensional image D is acquired, the correspondence relationship acquisition unit 22 aligns the three-dimensional images B and D to calculate a transformation function $T_{DB}$ indicating the correspondence relationship between the pixels of the three-dimensional images B and D, calculates a mapping function $M_{DS'}$ ($=T_{DB} \cdot M_{BS'}$) indicating the correspondence relationship between the three-dimensional image D and the auxiliary coordinate system S', using the operation of the calculated transformation function $T_{DB}$ and the mapping function $M_{BS'}$, and stores the mapping function $M_{DS'}$ in the storage unit 24 since the subject in the three-dimensional image D does not overlay any of the subjects in the three-dimensional images A and C and at least partially overlaps the subject in the three-dimensional image B (4). Therefore, a positional relationship $T_{AC}$ between the three-dimensional images A and C can be calculated using the operation of the mapping functions $M_{AS}$ and $M_{CS}$ for the three-dimensional images A and C which are stored in the storage unit 24, and a positional relationship $T_{BD}$ between the three-dimensional images B and D can be calculated using the operation of the mapping functions $M_{BS'}$ and $M_{DS'}$ for the three-dimensional images B and D which are stored in the storage unit 24.

Then, when the three-dimensional image E is acquired, the correspondence relationship acquisition unit 22 aligns the three-dimensional images C and E to calculate a transformation function $T_{EC}$ indicating the correspondence relationship between the pixels of the three-dimensional images C and E, calculates a mapping function $M_{ES}$ ($=T_{EC} \cdot M_{CS}$) indicating the correspondence relationship between the three-dimensional image E and the common coordinate system S, using the operation of the calculated transformation function $T_{EC}$ and the mapping function $M_{ES}$, and stores the mapping function $M_{ES}$ in the storage unit 24 since the subject in the three-dimensional image E at least partially overlaps the subject in the three-dimensional image C. Then, since the subject in the three-dimensional image E at least partially overlaps the subject in the three-dimensional image B or D, the correspondence relationship acquisition unit 22 calculates mapping functions $M_{BS}$ ($=T_{BE} \cdot M_{ES} = T_{DB}^{-1} \cdot T_{DE} \cdot M_{ES}$) and $M_{DS}$ ($=T_{DE} \cdot M_{ES}$) indicating the correspondence relationships between the three-dimensional images B and D and the common coordinate system S, on the basis of the correspondence relationships between the three-dimensional images B and D and the three-dimensional image E, and stores the calculated mapping functions $M_{BS}$ and $M_{DS}$ in the storage unit 24, instead of the mapping functions $M_{BS'}$ and $M_{DS'}$ (5). In this way, the positional relationships between the five three-dimensional images A, B, C, D, and E can be calculated by the operation of the mapping functions for the three-dimensional images which are stored in the storage unit 24.

As described above, according to the image processing system 1 of this embodiment, in the image management server 20, the correspondence relationship setting unit 21 defines the three-dimensional common coordinate system S and sets the first correspondence relationship between each pixel of the first three-dimensional image which has at least a portion of the human body as the subject and the coordinates on the common coordinate system S. The correspondence relationship acquisition unit 22 aligns the first three-dimensional image and the second three-dimensional image, which has at least a portion of the human body as the subject that at least partially overlaps the subject in the first three-dimensional image, to calculate the correspondence relationship between the pixels of the first three-dimensional image and the second three-dimensional image, calculates the second correspondence relationship between each pixel of the second three-dimensional image and the coordinates on the common coordinate system S, on the basis of the calculated correspondence relationship and the set first correspondence relationship, and stores the first correspondence relationship and the second correspondence relationship in the storage unit 24. Therefore, when the positional relationship between the three-dimensional images is calculated later, for example, the positional relationship acquisition unit 23 can calculate the positional relationship between target three-dimensional images, using the operation of the correspondence relationships (mapping functions) between the three-dimensional images and the common coordinate system S stored in the storage unit.

In particular, in the method according to the related art which defines other three-dimensional images using a reference image, in some cases, it is difficult to define the transformation function according to the three-dimensional image and to calculate the positional relationship between the reference image and other three-dimensional images. In contrast, in the image processing device, method, and program according to the invention, each captured three-dimensional image of the patient is defined using the coordinate system which can define a three-dimensional space with a sufficient size to include the entire body of the patient. Therefore, it is possible to define the correspondence relationship between each three-dimensional image and the coordinate system, regardless of the range of the subject or the size of the image, and to calculate the positional relationship between the three-dimensional image and other three-dimensional images, using the defined correspondence relationship. That is, it is possible to effectively calculate the positional relationship between a plurality of three-dimensional images.

In the above-described embodiment, the image management server 20 has a function which calculates the positional relationship between the three-dimensional images, using the operation of the correspondence relationships (mapping functions) between the three-dimensional images and the common coordinate system S, in response to, for example, a request from the client terminal 30, and provides information about the calculated positional relationship to the client terminal 30 which is a request source. However, this function is not necessarily required and may be provided if necessary. For example, the image management server 20 may have a function which provides information about the correspondence relationship (mapping function) required to acquire the positional relationship between the three-dimensional images, instead of the above-mentioned function.

What is claimed is:

1. An image processing device comprising:
correspondence relationship setting means for setting a three-dimensional common coordinate system and for setting a first correspondence relationship between each pixel of a first three-dimensional image which has at least a portion of a human body as a subject and coordinates on the common coordinate system; first correspondence relationship acquisition means for aligning a second three-dimensional image, which has at least a portion of the human body as a subject that at least partially overlaps the subject in the first three-dimensional image, with the first three-dimensional image to calculate a correspondence relationship between pixels of the first three-dimensional image and the second three-dimensional image, and for calculating a second correspondence relationship between each pixel of the second three-dimensional image and coordinates on the common coordinate system, on the basis of the calculated correspondence relationship and the set first correspondence relationship; storage means for storing the first correspondence relationship and the second correspondence relationship; obtaining means for obtaining the first correspondence relationship and the second correspondence relationship; and second correspondence relationship acquisition means for obtaining a correspondence relationship between the first three-dimensional image and the second three-dimensional image based on the first correspondence relationship and the second correspondence relationship; wherein, when a subject in a new three-dimensional image whose correspondence relationship with coordinates on the common coordinate system has been stored in the storage means as least partially overlaps the subject in the existing three-dimensional image whose correspondence relationship with coordinates on the auxiliary coordinate system has been stored in the storage means, the correspondence relationship acquisition means aligns the existing three-dimensional image with the new three-dimensional image to calculate a correspondence relationship between pixels of the existing three-dimensional image and the new three-dimensional image, and calculates another correspondence relationship between each pixel of the existing three-dimensional image and coordinates on the common coordinate system, on the basis of the calculated correspondence relationship and the correspondence relationship between the new three-dimensional image and the coordinates on the common coordinate system stored in the storage means, and the storage means stores the calculated another correspondence relationship, instead of the stored correspondence relationship between the existing three-dimensional image and the coordinates on the auxiliary coordinate system.

2. The image processing device according to claim 1, further comprising:
positional relationship acquisition means for calculating a positional relationship between the three-dimensional images whose correspondence relationship with the coordinates on the common coordinate system has been stored in the storage means, using an operation of the correspondence relationships between the three-dimensional images stored in the storage means.

3. The image processing device according to claim 1, wherein the correspondence relationship acquisition means aligns a new three-dimensional image, which has at least a portion of the human body as a subject that at least partially overlaps the subject in the existing three-dimensional image whose correspondence relationship has been stored in the storage means, with the existing three-dimensional image to calculate a correspondence relationship between pixels of the existing three-dimensional image and the new three-dimensional image, and calculates a third correspondence relationship between each pixel of the new three-dimensional image and coordinates on the common coordinate system, on the basis of the calculated correspondence relationship and the correspondence relationship of the existing three-dimensional image stored in the storage means, and the storage means stores the calculated third correspondence relationship.

4. The image processing device according to claim 3, wherein the correspondence relationship acquisition means calculates a correspondence relationship between a portion of the entire new three-dimensional image in which the subject overlaps the subject in the existing three-dimensional image and coordinates on the common coordinate system, using an operation of at least portions of the calculated correspondence relationship between the pixels of the existing three-dimensional image and the new three-dimensional image and the correspondence relationship of the existing three-dimensional image stored in the storage means, and the correspondence relationship acquisition means extrapolates the calculated correspondence relationship of the overlap portion to calculate a correspondence relationship between a portion of the entire new three-dimensional image in which the subject does not overlap the subject in the existing three-dimensional image and coordinates on the common coordinate system.

5. The image processing device according to claim 1, wherein the correspondence relationship setting means sets a correspondence relationship in which a relative positional relationship between the pixels of the first three-dimensional image is the same as a relative positional relationship between the coordinates associated with each of the pixels on the common coordinate system as the first correspondence relationship.

6. The image processing device according to claim 2, wherein the correspondence relationship setting means defines a three-dimensional auxiliary coordinate system and sets a fourth correspondence relationship between each pixel of a fourth three-dimensional image having a subject which does not overlap any subjects in the three-dimensional images whose correspondence relationship with the coordinates on the common coordinate system has been stored in the storage means and coordinates on the auxiliary coordinate system, the correspondence relationship acquisition means aligns a fifth three-dimensional image having a subject which does not overlap any subjects in the three-dimensional images whose correspondence relationship with the coordinates on the common coordinate system has been stored in the storage means and at least partially overlaps the subject in the fourth three-dimensional image to calculate a correspondence relationship between pixels of the fourth three-dimensional image and the fifth three-dimensional image, and calculates a fifth correspondence relationship between each pixel of the fifth three-dimensional image and coordinates on the auxiliary coordinate system, on the basis of the calculated correspondence relationship and the set fourth correspondence relationship, the storage means stores the fourth correspondence relationship and the fifth correspondence relationship, and the positional relationship acquisition means calculates a positional relationship between the three-dimensional images whose correspondence relationship with the coordinates on the common coordinate system has not been stored and whose correspondence relationship with coordinates on the auxiliary coordinate system has been stored, using an operation of the correspondence relationships between the three-dimensional images and the coordinates on the auxiliary coordinate system which are stored in the storage means.

7. The image processing device according to claim 6, wherein, when a subject in a new three-dimensional image whose correspondence relationship with coordinates on the common coordinate system has been stored in the storage means at least partially overlaps the subject in the existing three-dimensional image whose correspondence relationship with coordinates on the auxiliary coordinate system has been stored in the storage means, the correspondence relationship acquisition means aligns the existing three-dimensional image with the new three-dimensional image to calculate a correspondence relationship between pixels of the existing three-dimensional image and the new three-dimensional image, and calculates a sixth correspondence relationship between each pixel of the existing three-dimensional image and coordinates on the common coordinate system, on the basis of the calculated correspondence relationship and the correspondence relationship between the new three-dimensional image and the coordinates on the common coordinate system stored in the storage means, and the storage means stores the calculated sixth correspondence relationship, instead of the stored correspondence relationship between the existing three-dimensional image and the coordinates on the auxiliary coordinate system.

8. An image processing method that is performed by an image processing device including correspondence relationship setting means, first correspondence relationship acquisition means, storage means, obtaining means, and second correspondence relationship acquisition means, the method comprising:

allowing the correspondence relationship setting means to set a three-dimensional common coordinate system and to set a first correspondence relationship between each pixel of a first three-dimensional image which has at least a portion of a human body as a subject and coordinates on the common coordinate system;

allowing the first correspondence relationship acquisition means to align a second three-dimensional image, which has at least a portion of the human body as a subject that at least partially overlaps the subject in the first three-dimensional image, with the first three-dimensional image to calculate a correspondence relationship between pixels of the first three-dimensional image and the second three-dimensional image, and to calculate a second correspondence relationship between each pixel of the second three-dimensional image and coordinates on the common coordinate system, on the basis of the calculated correspondence relationship and the set first correspondence relationship;

allowing the storage means to store the first correspondence relationship and the second correspondence relationship;

obtaining means for obtaining the first correspondence relationship and the second correspondence relationship; and second correspondence relationship acquisition means for obtaining a correspondence relationship between the first three-dimensional image and the second three-dimensional image based on the first correspondence relationship and the second correspondence relationship.

9. A computer readable non transitory recording medium having an image processing program recorded therein, the image processing program causing a computer to function as:

correspondence relationship setting means for setting a three-dimensional common coordinate system and for setting a first correspondence relationship between each pixel of a first three-dimensional image which has at least a portion of a human body as a subject and coordinates on the common coordinate system;

first correspondence relationship acquisition means for aligning a second three-dimensional image, which has at least a portion of the human body as a subject that at least partially overlaps the subject in the first three-dimensional image, with the first three-dimensional image to calculate a correspondence relationship between pixels of the first three-dimensional image and the second three-dimensional image, and for calculating a second correspondence relationship between each pixel of the second three-dimensional image and coordinates on the common coordinate system, on the basis of the calculated correspondence relationship and the set first correspondence relationship;

storage means for storing the first correspondence relationship and the second correspondence relationship;

obtaining means for obtaining the first correspondence relationship and the second correspondence relationship; and second correspondence relationship acquisition means for obtaining a correspondence relationship between the first three-dimensional image and the second three-dimensional image based on the first correspondence relationship and the second correspondence relationship.

10. The image processing device according to claim 3, wherein the correspondence relationship acquisition means calculates a correspondence relationship between a portion of the entire new three-dimensional image in which the subject overlaps the subject in the existing three-dimensional image and coordinates on the common coordinate system, using an operation of at least portions of the calculated correspondence relationship between the pixels of the existing three-dimensional image stored in the storage means.

11. The image processing device according to claim 10, wherein the correspondence relationship acquisition means extrapolates the calculated correspondence relationship of the overlap portion to calculate a correspondence relationship between a portion of the entire new three-dimensional image and coordinates on the common coordinate system.

12. The image processing device according to claim 2, wherein the correspondence relationship setting means defines a three-dimensional auxiliary coordinate system and sets a fourth correspondence relationship between each pixel of a fourth three-dimensional image having a subject which does not overlap any subjects in the three-dimensional images whose correspondence relationship with the coordinates on the common coordinate system has been stored in the storage means and coordinates on the auxiliary coordinate system.

13. The image processing device according to claim 12, wherein the correspondence relationship acquisition means aligns a fifth three-dimensional image having a subject which does not overlap any subjects in the three-dimensional images whose correspondence relationship with the coordinates on the common coordinate system has been stored in the storage means and at least overlaps the subject in the fourth three-dimensional image to calculate a correspondence relationship between pixels of the fourth three-dimensional image and the fifth three-dimensional image, and calculates a fifth correspondence relationship between each pixel of the fifth three-dimensional image and coordinates on the auxiliary coordinate system, on the basis of the calculated correspondence relationship and the set fourth correspondence relationship.

14. The image processing device according to claim 13, the positional relationship acquisition means calculates a positional relationship between the three-dimensional images whose correspondence relationship with the coordinates on the common coordinate system has not been stored and whose correspondence relationship with coordinates on the auxiliary coordinate system has been stored.

* * * * *